US012606800B2

(12) United States Patent
Catapano et al.

(10) Patent No.: US 12,606,800 B2
(45) Date of Patent: Apr. 21, 2026

(54) BIOREACTOR, APPARATUS AND PROCESS FOR IN VITRO CULTURE OF REPRODUCTIVE TISSUES, AND THE LIKE

(71) Applicants: Gerardo Catapano, Naples (IT);
Roberto Gualtieri, Positano (IT);
Riccardo Talevi, Vietri sul Mare (IT)

(72) Inventors: Gerardo Catapano, Naples (IT);
Roberto Gualtieri, Positano (IT);
Riccardo Talevi, Vietri sul Mare (IT)

( * ) Notice: Subject to any disclaimer, the term of this patent is extended or adjusted under 35 U.S.C. 154(b) by 443 days.

(21) Appl. No.: 18/037,019

(22) PCT Filed: Nov. 15, 2021

(86) PCT No.: PCT/IB2021/060556
§ 371 (c)(1),
(2) Date: May 15, 2023

(87) PCT Pub. No.: WO2022/101874
PCT Pub. Date: May 19, 2022

(65) Prior Publication Data
US 2023/0416685 A1 Dec. 28, 2023

(30) Foreign Application Priority Data
Nov. 13, 2020 (IT) ......................... 102020000027290

(51) Int. Cl.
*C12N 5/071* (2010.01)
*C12M 1/00* (2006.01)
*C12M 1/12* (2006.01)
*C12M 1/34* (2006.01)
*C12M 3/00* (2006.01)

(52) U.S. Cl.
CPC ........... *C12N 5/0682* (2013.01); *C12M 21/08* (2013.01); *C12M 25/04* (2013.01); *C12M 29/10* (2013.01); *C12M 41/16* (2013.01)

(58) Field of Classification Search
CPC ..... C12N 5/0682; C12M 21/08; C12M 25/04; C12M 29/10; C12M 41/16; C12M 25/06
See application file for complete search history.

(56) References Cited

U.S. PATENT DOCUMENTS

| | | | |
|---|---|---|---|
| 2010/0075293 A1 | 3/2010 | Chang et al. | |
| 2022/0204905 A1* | 6/2022 | Karnieli | ................ C12M 29/18 |

FOREIGN PATENT DOCUMENTS

| | | | |
|---|---|---|---|
| EP | 2151491 A2 | 2/2010 | |
| FR | 2971255 A1 | 8/2012 | |
| WO | WO-2005056747 A2 * | 6/2005 | ........... C12M 25/14 |

OTHER PUBLICATIONS

International Search Report for PCT/IB2021/060556 dated Mar. 16, 2022 (2 pages).

* cited by examiner

*Primary Examiner* — Aaron J Kosar
(74) *Attorney, Agent, or Firm* — Tutunjian & Bitetto, P.C.

(57) ABSTRACT

A bioreactor for the in vitro culture of reproductive tissues and the like in perifusion mode, including a first component and a second component, mutually connected, which define between them at least one culture chamber; the former component includes an inlet port for introducing a culture medium into the culture chamber, while the latter component includes an outlet port, to allow the culture medium out of the culture chamber. The bioreactor includes at least one porous medium, provided inside the culture chamber, able to mechanically support fragments of reproductive tissue, and networks, positioned above and below the fragments of reproductive tissue, with reference to the vertical or substantially vertical position of use of the bioreactor.

13 Claims, 6 Drawing Sheets

BIOREACTOR, APPARATUS AND PROCESS FOR IN VITRO CULTURE OF REPRODUCTIVE TISSUES, AND THE LIKE

TECHNICAL FIELD OF THE INVENTION

The present invention relates to a bioreactor, an apparatus and a process for in vitro culture of fragments of reproductive tissues such as ovarian tissues, endometrial tissues and the like.

The bioreactor, apparatus and process can be used for a wide range of fragment cultures, including, but not limited to, ovarian, human or animal endometrial tissues, either fresh or cryopreserved.

DESCRIPTION OF THE PRIOR ART

Various types of bioreactor are known for in vitro culture of cells for the engineering of biological substitutes of tissues and fragments of primary tissues, human and otherwise.

Some of these bioreactors are of the so-called perfusion type.

They typically comprise a culture chamber open on two opposite sides, at which an inlet opening and an outlet opening for a liquid culture medium are provided-respectively.

The latter has the function of allowing the culture of tissue to be carried out in a controlled environment, and of perfusing the tissues with the appropriate nutrients and biochemical stimuli necessary for their growth and differentiation.

Inside the culture chamber there is a so-called tissue scaffold, that is a structure able to accommodate the characteristic tissue cells or fragments of tissue in the culture.

It is usually a very complex geometry structure, that is, a sort of often three-dimensional scaffolding, which can vary in terms of chemical-physical nature, and which mechanically supports the cellular architecture or the fragments of tissue.

In the most typical applications, such scaffolds are made of biocompatible polymeric porous material.

Normally the bioreactor is inserted, within a closed circuit, inside a special system for culture medium feeding.

In particular, the inlet opening and the outlet opening of the bioreactor are connected to respective portions of the aforementioned feeding system duct.

Thus, within the culture chamber of the bioreactor, the culture medium enters and flows around (perifusion mode) or through (perfusion mode) or around and through (mixed mode) the tissue fragments or scaffold, thereby perfusing with liquid, by capillary action, the cells contained within the tissue fragments or the scaffold, and then leaves the bioreactor; in this way continuous circulation is created which guarantees a constant exchange of liquid and of the species dissolved in it.

The perfusion bioreactors described are used very frequently for the culture of certain types of cells in tissue or tissue substitutes, such as for example bone substitutes, and others; in these applications, these bioreactors allow fairly satisfactory results to be obtained.

However, it has been observed that, in cultures of different and specific types of cells or tissues, the bioreactors designed in this way have a margin for improvement in different ways.

For example, within the scope of applications for the in vitro culture of reproductive tissues, such as ovarian or endometrial tissue, or applications for in vitro tissue activation followed by in vivo implant/transplant, or even further applications such as those for the study of the interactions between the endometrium and the embryo in vitro, and for the in vitro evaluation of the toxicity of biological, chemical and medicinal substances, the available bioreactors having the previously described characteristics are not considered to be fully satisfactory.

In particular, the aforementioned bioreactors have shown deficiencies in the perfusion and transfer of nutrients and dissolved oxygen to the cells contained in the tissue fragments or in the scaffold, and also in relation to the possibility of controlling, in a precise and detailed way, the evolution cell growth within the tissue fragments or the scaffold itself.

SUMMARY OF THE INVENTION

The technical task of the present invention is therefore to improve the state of the art in the field of in vitro culture of reproductive tissues, such as ovarian tissues, endometrial tissues and the like.

Within the scope of this technical task, it is an object of the present invention to provide a bioreactor, an apparatus and a process for the in vitro culture of reproductive tissues and the like which allow the aforementioned drawbacks to be overcome.

Another object of the present invention is to provide a bioreactor, an apparatus and a process for the in vitro culture of reproductive tissues, and the like, which are more efficient as regards the controlled transfer of nutrients and dissolved oxygen into the culture medium and of biomechanical stimuli to the culture tissues.

Another object of the present invention is to make available a bioreactor, an apparatus and a process for the in vitro culture of reproductive tissues, and the like, improved and perfected in relation to the possibility of controlling, in a precise and accurate way, the evolution of cultured tissues growth.

A further object of the present invention is to provide a bioreactor, an apparatus and a process for the in vitro culture of reproductive tissues, and the like, which are constructively simple and economical.

Another object of the present invention is to build a bioreactor, an apparatus and a process for the in vitro culture of reproductive tissues, and the like, which are simple, practical and effective to use.

This task and these objects are all achieved by a bioreactor for in vitro culture of reproductive tissues, and the like, according to the present application.

The bioreactor comprises a first component and a second component, mutually connected, which define between them at least one culture chamber.

The first component comprises an inlet port for introducing a culture medium into the culture chamber, while the second component comprises an outlet port, to allow the culture medium out of the culture chamber.

Furthermore, the bioreactor comprises at least one porous medium, provided inside the culture chamber, able to mechanically support fragments of reproductive tissue, and possibly networks, positioned above and below the fragments of reproductive tissue, with reference to the vertical or substantially vertical position of use of the bioreactor.

The networks are substantially flat structures made from intertwined threads or fibres between which openings are formed (called meshes or pores), installed in the bioreactor so that they adhere to the fragments. In the bioreactor they perform the following functions: together with the porous support, they keep the fragments of reproductive tissue, in a safe way, in respective controlled positions inside the culture chamber; their structure is such as to exert mechanical stimuli directly applied to the tissues in unison with the actuators possibly present in the first component of the bioreactor; the width and density of their meshes is such as to be able to precisely adjust the speed and distribution in the chamber of the culture medium that makes light contact to them, as well as the fluid dynamic stimuli indirectly applied to the tissues.

This solution allows to considerably increase the efficiency of the bioreactor in relation to the transfer of nutrients to the cultured tissues, compared to currently known solutions.

Furthermore, the tissue fragments, kept in their respective correct culture positions but in any case, within their surfaces, can be more easily and thoroughly controlled in their evolution.

This task and these objects are also all achieved by an apparatus for in vitro culture of reproductive tissues, and the like, according to the present application.

The apparatus comprises at least one bioreactor, according to the present invention, and a circuit for the circulation of a culture medium inside the bioreactor, and at least one pump, fitted along the aforementioned circuit, for activating the circulation of the culture medium inside the bioreactor.

The apparatus also comprises at least one tank, which contains the culture medium, installed along the aforementioned circuit, and at least one gas exchanger, installed along the circuit, for allowing an effective exchange of gas with the culture medium.

This task and these objects are also all achieved by a process for in vitro culture of reproductive tissues, and the like, according to the present application.

The process comprises the steps of providing an apparatus, for the in vitro culture of reproductive tissue fragments, according to the present invention, comprising, in turn, at least one bioreactor as previously described.

The process also comprises a step in which fragments of reproductive tissue are placed inside the culture chamber of the bioreactor, positioning them on the porous support, interposed between the first network and the second network, at mutually predetermined distances.

The process then includes a start-up step of the apparatus, in which the bioreactor is fed culture medium, so that the latter flows into the culture chamber, and comes into light contact, in a controlled way, with the surfaces of fragments of reproductive tissue, while this is possibly subject to direct biomechanical stimuli through interaction with the components of the bioreactor.

By doing so, and in particular thanks to the positioning of the tissue fragments between the two bioreactor mesh networks, high efficiency of the direct and fluid dynamic biomechanical stimuli is obtained, as well as in the transfer/administration of nutrients and gases to the tissues.

At the same time, the free surfaces of the tissue fragments, inside the culture chamber, allow the growth and evolution of the same tissues to be modulated during the culture period.

The present application refers to preferred and advantageous embodiments of the invention.

BRIEF DESCRIPTION OF DRAWINGS

These and additional advantages will be better understood by any technician skilled in the art from the following description and accompanying drawings, provided by way of non-limiting example, in which.

DETAILED DESCRIPTION OF THE INVENTION

Figure 1:
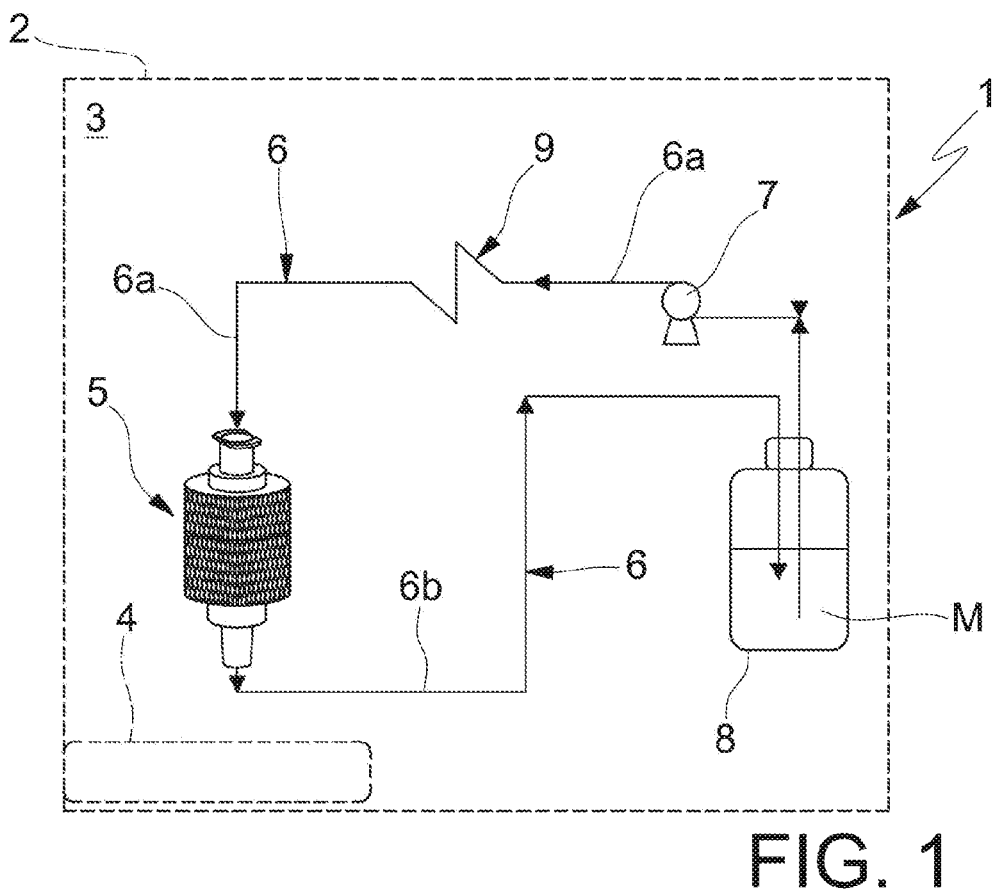
FIG. 1 is a schematic view of an apparatus for the in vitro culture of reproductive tissues according to the present invention.

With reference to FIG. 1, the reference number 1 globally indicates a version of an apparatus for in vitro culture of reproductive tissues according to the present invention.

Although the term tissue is often used to indicate both natural tissue (or a fragment thereof) and a biological substitute for natural fabric (or a fragment thereof), there are great structural and functional differences between the two, especially in the early stages of culture of the biological substitute.

A natural tissue generally consists of various cells, which give the tissue a specific biological function, immersed in a generally very dense extracellular matrix made up of natural polymers and other cells.

Without going into biological considerations, the structure of a natural tissue fragment is so dense that it prevents a significant convective flow of a fluid forced through the tissue by a pressure gradient fluid dynamically generated on the sides of a small tissue fragment, unless the vessels in the tissue are anastomosed to the tubes that carry fluid to the tissue.

A biological (or bioengineered) substitute for a tissue is generally produced by spreading some of the cells typically found in natural tissue in a porous three-dimensional structure (the scaffold) which replaces the mechanical support role played by the extracellular matrix of natural tissue.

During the culture of a biological substitute in a bioreactor, an attempt is made at creating an environment around the cells that enhances their proliferation up to the cellular concentrations that occur in natural tissue, and which enhances its differentiation so that some cells can produce their own extracellular matrix to replace that of the scaffold.

For this reason, early on in the culture, the hydraulic permeability (i.e. the fluid flow per unit of thickness of the construct and unit of pressure difference on the two sides of the fragment) of the construct (i.e. the scaffold spread with the cells) is very high. Under such conditions, many bioreactors are designed to enhance the flow of culture medium through the fragment and the conveying of nutrients and dissolved oxygen to the cells inside it, ensuring their survival.

As cells proliferate and differentiate, the hydraulic permeability of the construct decreases until it becomes so small that it effectively nullifies the flow of culture medium that perfuses the construct, so that the conveying of solutes throughout of the fragment width occurs only by diffusion (i.e. due to a difference in concentration). Under these conditions, the culture medium flows preferentially around the fragments if there are alternative routes of lower hydraulic resistance, and the above-mentioned bioreactors only allow to reduce the resistance to the conveying of nutrients and dissolved gases outside the fragment.

If there are no alternative routes to the conveying of the culture medium through the construct, the pressures that build up upstream of the fragment can cause it to be crushed, for example if the scaffold is made from a hydrogel.

This being understood, it should be noted that the apparatus 1 according to the present invention is intended exclusively for the culture of fragments of natural reproductive tissue, e.g. ovarian or endometrial tissue.

In FIG. 1, the apparatus 1 is represented schematically, with an indication of essential components.

In the version of the invention of FIG. 1, the apparatus 1 comprises an incubator 2. As better clarified below, the presence of incubator 2 is optional inside the apparatus 1.

The incubator 2 comprises a chamber 3; chamber 3 is thermally insulated.

Furthermore, the chamber 3 is provided with an adjustable heater and a controller of the partial pressure of oxygen and carbon dioxide in gas phase 4, which keeps it at a temperature and at concentrations of oxygen and carbon dioxide in the culture medium that are optimal for the in vitro culture according to the present invention. According to an aspect of the invention, the apparatus 1 comprises a bioreactor 5; the bioreactor 5 is located inside the insulated chamber 3 of the incubator 2.

According to another aspect of the invention, the bioreactor 5 is designed and configured to operate in perifusion mode.

This mode has the purpose of minimising the resistance to the conveying of solutes outside the fragments of dense natural reproductive tissue. The apparatus 1 also comprises a circuit 6 for the circulation of a culture medium M inside the bioreactor 5, and at least one pump 7, mounted along the circuit 6, for activating the aforementioned circulation of the culture medium M inside the bioreactor 5, through the aforementioned circuit 6. The apparatus 1 also comprises at least one tank 8, which contains the culture medium M.

The tank 8 is installed along the circuit 6, which allows the circulation of the culture medium M inside the bioreactor 5.

More in detail, the circuit 6 comprises a duct 6a for directing the culture medium towards the bioreactor 5, along which the pump 7 is installed, which takes the culture medium M from the tank 8.

Furthermore, the circuit 6 comprises a return duct 6b, which conveys the culture medium M, coming from the bioreactor 5, into the tank 8.

According to another aspect of the invention, the apparatus 1 comprises a gas exchanger device 9, installed along the circuit 6.

The exchanger 9 is adapted to allow the exchange of gas (such as, but not limited to, oxygen or carbon dioxide) with the culture medium M.

In a preferred embodiment of the invention, the exchanger 9 comprises (or consists of) one or more tubes permeable to gases but not to liquids, which allow the gaseous oxygen and carbon dioxide of the environment inside chamber 3 of the incubator 2 to be exchanged with the culture medium M.

Figure 7:
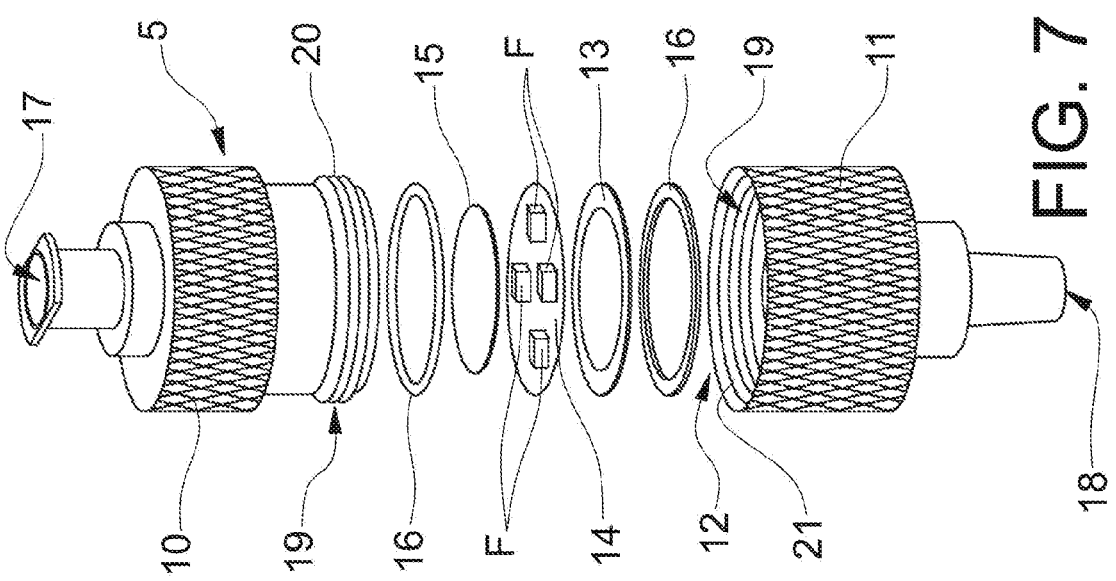
FIG. 7 is an exploded axonometric view of a bioreactor which is part of the versions of the apparatuses of FIGS. 1, 2.

The bioreactor 5—shown in detail in FIG. 7—comprises a first component 10 and a second component 11, mutually connected, which define between them at least one culture chamber 12.

The culture chamber 12 has a substantially cylindrical shape, arranged with a vertical axis, and has inlet and outlet sections which can have, but not limited to, truncated cone, or hyperboloid, or discoid, or similar shapes.

In the culture chamber 12, fragments F of reproductive tissue can be cultured in common, in controlled positions. The bioreactor 5 also comprises at least one porous support 13, provided inside the culture chamber 12.

The porous support 13 is able to support the fragments F of reproductive tissue inside the culture chamber 12, allowing, at the same time, the correct flow of the culture medium M inside the bioreactor 5.

The bioreactor 5 also comprises two networks 14, 15, provided inside the culture chamber 12.

The networks 14, 15 are positioned above and below the fragments F of reproductive tissue, with reference to the vertical or substantially vertical position of use of the bioreactor 5, shown in FIG. 1.

More in detail, the bioreactor 5 comprises a first network 14, adapted to be positioned under the fragments F of reproductive tissue (and therefore above the porous support 13).

Furthermore, the bioreactor 5 comprises a second network 15, adapted to be positioned over the fragments F of reproductive tissue.

The networks 14, 15 have the function of maintaining the fragments F of reproductive tissue in respective controlled positions, and/or of exerting a biomechanical stimulation action on the tissue, and/or of allowing the culture medium to flow according to controlled speed and trajectories with respect to the tissue fragments F. In other words, thanks to the positioning of the aforementioned networks 14, 15, the bioreactor 5 of the apparatus 1 according to the present invention is a continuous flow device of the so-called "packed bed" type, wherein the tissue fragments F are kept immobilized, or fixed, in certain areas of the bioreactor 5, unlike other bioreactors of the so-called "fluidized bed" type wherein the tissue fragments F are kept in suspension by the flowing of the culture medium.

The first network 14 and/or the second network 15 can be made using hollow fibres, wherein a heating or cooling liquid flows to exchange heat and control the temperature of the culture medium inside the bioreactor (5).

Alternatively, or in combination with the last mentioned solution, the first network 14 and/or the second network 15 can be made using gas-permeable hollow fibres, wherein a gas flows containing predetermined concentrations of gaseous oxygen and carbon dioxide, to exchange these gases and monitor their dissolved concentrations in the culture medium inside the bioreactor 5.

It is also specified that the networks 14, 15 are shaped and configured in such a way as to: maintain a plurality of fragments F of reproductive tissue, inside the culture chamber 12, in respective predetermined spatial positions, and at suitable mutual distances; to make the culture medium M flow according to controlled speed and trajectories along the surfaces of the fragments F so as to avoid the formation of preferential or by-pass flows that minimize the contact of the culture medium with the tissue fragments F.

For this purpose, the meshes (or the openings or pores between the fibres or the threads) of the networks 14, 15 must have smaller dimensions than those of the fragments F. i.e. less than 1 mm, and preferably between 200 microns and 500 microns.

The networks 14, 15 also have the function of exerting a direct mechanical stress (by deformation) on the fragments F in unison with the actuators A present in the inlet section to the bioreactor, whether they are passive (for example ribs or channels whose edges protrude from the internal wall of the inlet and outlet sections of the bioreactor) or active (for example pressure surfaces implemented with stepper motors).

To this End:

the thickness of the networks 14, 15 must be such that, when added to the dimensions (or displacements) of the actuators A, they cause the tissue to be subjected to predetermined deformations (preferably less than 20%);

the density of the meshes (or fibres, or threads) per surface unit of each network 14, 15 must allow the transmission of the deformations obtained (in unison with those of the passive or active actuators A) to all the cultured fabric fragments F in chamber 12.

In summary, the networks 14, 15 have the following functions:

maintain a plurality of fragments F of reproductive tissue, inside the culture chamber 12, in respective predetermined space positions, and at appropriate mutual distances;

distribute to all the tissue fragments F the mechanical stress generated by the actuators A in the inlet section of the culture chamber 12;

enhance motion of the culture medium M around the fragments F (in perifusion mode) together with any passive actuators A in the inlet section of the bioreactor, so as to ensure the exchange of nutrients, gases and dissolved biochemical signals between fragments and the culture medium, to stimulate them with fluid-dynamic efforts of controlled extent, and to avoid the formation of preferential or by-pass flows which minimise the contact of the culture medium M with the tissue fragments F;

allow easy recovery of tissue fragments F at the end of the culture; for this purpose, if used in pairs, the networks 14, 15 above and below the tissue fragments F can be partially sealed at the periphery and form a pocket in which the fragments F are trapped by weaving, gluing or other equivalent technique.

The networks 14, 15 can be made of any biocompatible and sterilizable material (e.g. polymers, metals, etc.) and can appear as semi-permeable networks, grids or membranes, and be produced starting from solid material or woven or unwoven fibres, starting from mono- or multifilament.

The porous support 13, the first network (0.14) and second network (15) are tightly packed between the first component 10 and the second component 11 of the bioreactor 5, with one or more interposed sealing gaskets 16, for example of the O-ring type, or another similar type.

The first component 10 can be made of any material, e.g. a polymer, metal, ceramic or other suitable materials.

The first component 10 comprises an inlet port 17, for introducing the culture medium M inside the bioreactor 5, in particular inside the culture chamber 12.

The inlet port 17 can have any geometry and/or position.

Furthermore, the first component 10 can comprise at least one flow distributor, of any geometry and/or material, which can have grooves, or the like, to channel the flow of culture medium M.

The second component 11 can be made of any material, for example a polymer, metal, ceramic or other suitable materials.

The second component 11 comprises an outlet port 18, to let the culture medium M out of the bioreactor 5 (in particular out of the culture chamber 12).

The outlet port 18 can have any geometry and/or position.

Furthermore, the second component 11 can comprise at least one manifold for the flow of the culture medium M towards the outlet port 18; the manifold may comprise grooves, or other similar elements.

The first component 10 and the second component 11 are mutually associated by means of connecting means 19.

The aforesaid connecting means 19 are preferably of the resolvable type, so as to be able to easily separate, when necessary, the first component 10 from the second component 11.

Typically, it may be necessary to separate the first component 10 from the second component 11 to insert the fragments F of reproductive tissue inside the culture chamber 12, or to remove them therefrom.

The connecting means 19 can be of the screw, bayonet type, or the like, without any particular limitations.

For example, the connecting means 19 can comprise an external thread 20 made in the first component 10, and a nut screw made in the second component 21, or vice versa.

According to a further aspect of the invention, the bioreactor 5 comprises one or more actuators A, provided inside the culture chamber 12.

The aforementioned actuators A have, mainly, the function of passively or actively applying stress to the fragments F of reproductive tissue, during culture, with controlled fluidic and/or mechanical stress, including (but not limited to) compressive or traction stress.

The one or more actuators A provided inside the culture chamber 12 can be of any type suitable for this type of application, without any particular limitations.

Figures 9, 10:
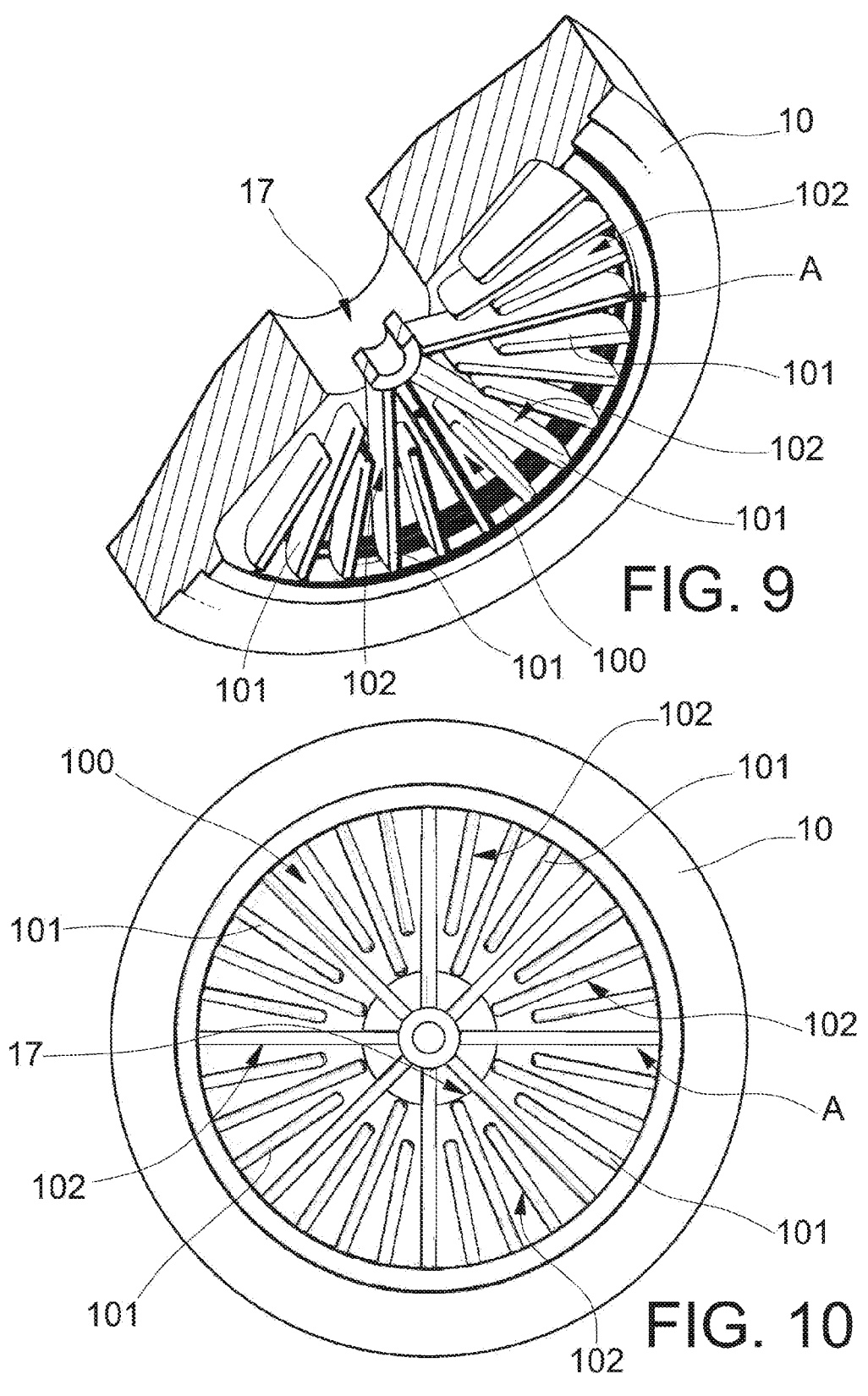
FIG. 9 is a schematic perspective view of the first component of the bioreactor, in another version of the invention.
FIG. 10 is a view from below of the first component of FIG. 9.

More in detail, as previously mentioned, these actuators A can be passive (for example ribs or channels whose edges protrude from the inside wall of the first component 10 of the bioreactor 5) or active (for example pressure surfaces actuated with stepper motors). More in detail, FIGS. 9, 10 refer to a version of the invention wherein the first component 10 of the bioreactor 5 comprises, along its internal wall 100, passive actuators A.

The latter comprise, in turn, ribs 101, arranged substantially in a radial pattern around the inlet port 17.

The ribs 101 define, between them, channels 102 along which the culture medium M, coming from the inlet port 17, flows in centrifugal directions.

The ribs 101 therefore have the dual function of exerting a mechanical pressure stress on the second network 15, and also of uniformly distributing the flow of the culture medium M.

The shaping and thickness of the meshes of the second network 15 in any case ensure the circulation of the culture medium M around the surface of the fragments F, despite the pressure exerted by the aforementioned ribs 101.

The inner wall 100 of the first component 10 can have a frusto-conical, hyperboloid, discoid, or similar shape.

Figure 11:
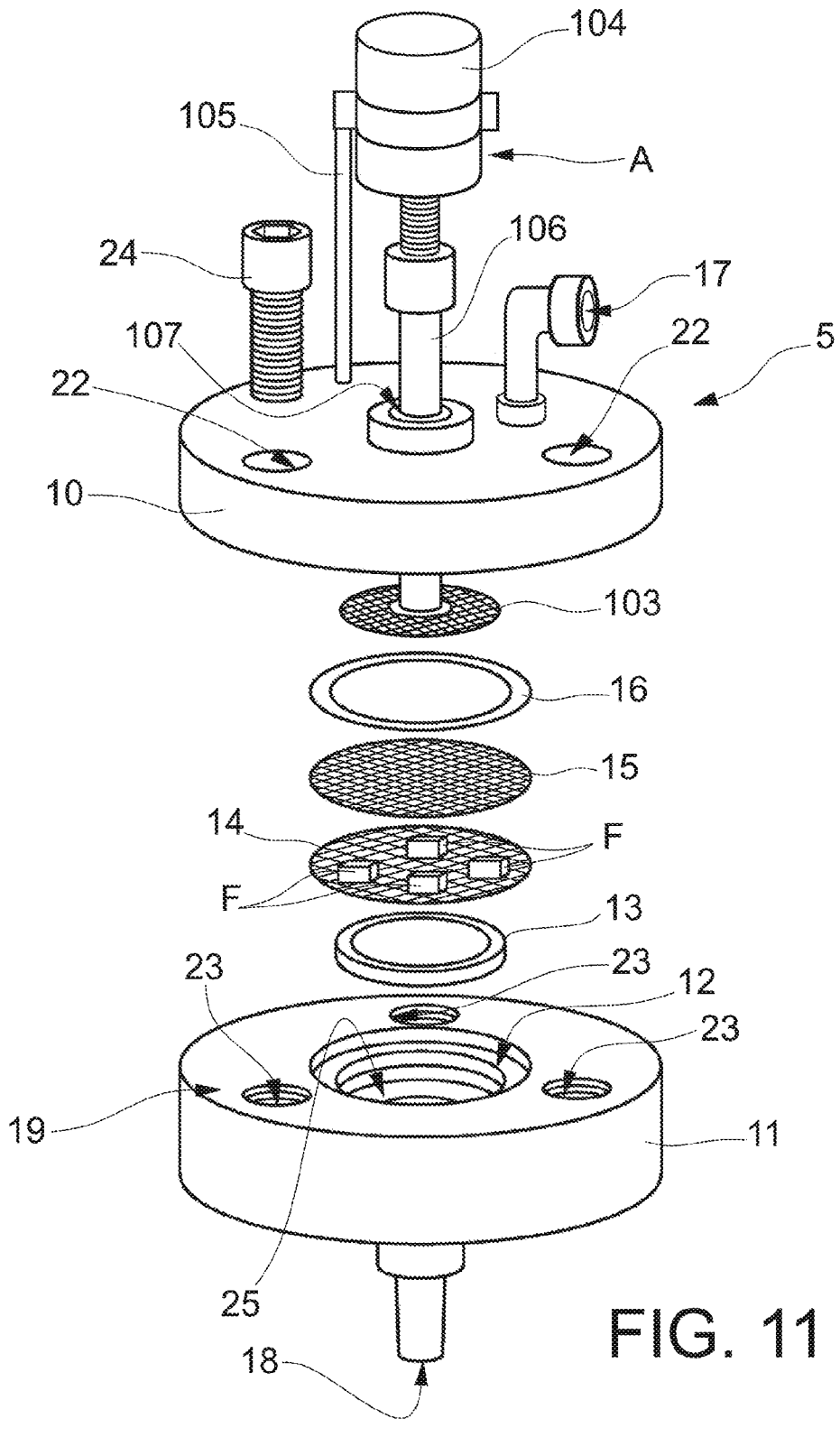
FIG. 11 is an exploded axonometric view of another version of the bioreactor according to the invention.

FIG. 11 instead refers to a version of the invention wherein the first component 10 of the bioreactor 5 comprises an active actuator A, which in turn comprises at least one pressure surface 103 driven by an electric motor 104, of the stepper type.

The aforementioned pressure surface 103 can comprise a mesh piston.

The electric motor 104 is associated with the upper external wall of the first component 10; for example, the electric motor 104 is supported by a bracket 105 connected to the upper outer wall of the first component 10.

A stem 106 is connected to the axle of the electric motor 104, passing through a special hole with a sealing element 107 provided in the first component 10, so as to enter into the culture chamber 12; the end of the stem 106 is in turn associated with the pressure surface 103, configured to exert a given amount of mechanical pressure stress on the second network 15, with a downward translational motion.

According to another aspect of the invention, the first component 10, or the second component 11, or both, are provided with means for heat exchange and for controlling the temperature of the bioreactor 5.

Said heat exchange and temperature control means can comprise, for example, a jacket, which contains the bioreactor 5, inside which a heating/cooling fluid flows, and/or a Peltier cell, or other similar devices.

FIG. 2 shows, again schematically, another embodiment of the apparatus 1 for the in vitro culture of reproductive tissues according to the present invention.

This embodiment differs from that of FIG. 1 in that the apparatus 1 is without an incubator.

The absence of the incubator is compensated by the fact that the apparatus 1 comprises a heat exchanger 30.

The heat exchanger 30 is inserted along the circuit 6 for the circulation of the culture medium M.

More in detail, the heat exchanger 30 is inserted, along the delivery duct 6a, immediately downstream of the gas exchanger 9, with reference to the circulation flow of the culture medium M.

The heat exchanger 30 maintains the temperature of the culture medium M within a predetermined range of optimal operation.

In this embodiment of the apparatus 1 the gas exchanger 9 is, by way of example but not limited to, a gas exchanger with hollow capillary membranes for blood oxygenation which allows, for example, culture medium M to be administered the gaseous oxygen supplied to the gas compartment of the exchanger by means of, but not limited to, a compressed gas cylinder.

Thanks to this measure, the incubator 2 and its respective adjustable heater 4, described in the previous embodiment, become unnecessary.

The heat exchanger 30 can be of any type suitable for this type of application (preferably of the insulated type).

The bioreactor 5 must also be adequately insulated.

FIG. 3 shows, again schematically, another version of the apparatus 1 for the in vitro culture of reproductive tissues according to the present invention.

This version differs from that of FIG. 1 for the shaping of the bioreactor 5.

Figure 8:
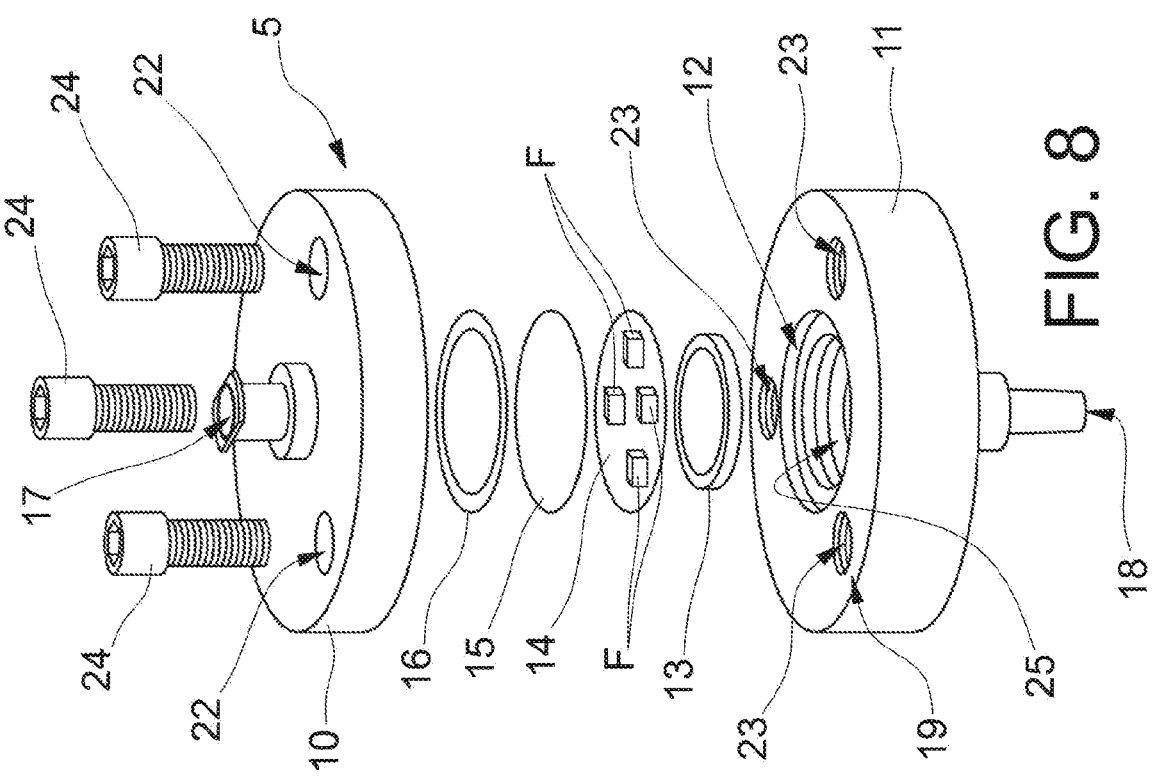
FIG. 8 is an exploded axonometric view of another version of bioreactor, which is part of the apparatus shown in FIGS. 3-6.

The bioreactor 5 of this version of the invention is shown in FIG. 8.

More in detail, in this version of the invention, compared to those previously described, the shaping and configuration of the first component 10 and of the second component 11 of the bioreactor 5 are different, and so is the shaping and configuration of the connecting means 19.

In fact, in this version, the first component 10 and the second component 11 both have a substantially hyperboloid or discoid shape.

The first component 10 comprises, in the centre, the inlet port 17 for the culture medium M.

The connection means 19 comprise, in the first component 10, a plurality of through holes 22, provided substantially at the periphery of the first component 10 (for example, three through holes 22 are provided).

The second component 11 comprises, in the centre, the outlet port 18 for the culture medium M.

Moreover, the connecting means 19 comprise, in the second component 11, a plurality of threaded holes 23, provided substantially at the periphery of the second component 11 (for example, three threaded holes 23 are provided).

The connecting means 19 also comprise screws 24, which engage in the through holes 22 of the first component 10, and in the corresponding threaded holes 23 of the second component 11.

Alternatively, the screws 24 can engage in through holes (made in place of the threaded holes 23) of the second component 11; the seal between the first component 10 and the second component 11 is ensured by nuts and any locking washers.

It is thus possible to constrain the first component 10 and the second component 11 to each other in a removable way, in order to be able to access the culture chamber 12 if needed.

The first component 10 and the second component 11 also comprise respective seats 25, made in the respective internal faces, in use, to house the perforated support plate 13, the first network 14, the second network 15, and one or more sealing gaskets 16. Thanks to the presence of these seats 25, which house all the internal components of the bioreactor 5, the internal faces of the first component 10 and of the second component 11 are perfectly matched, in an assembled configuration.

This version of the bioreactor 5, compared to those previously described, has different characteristics mainly as regards the separation of the first component 10 from the second component 11, which can take place without rotating one with respect to the other, but only by removing the screws 24.

This can be advantageous in certain configurations of the circuit 6, for example if removing the ducts 6a, 6b is not possible, or if twisting them to separate the two components 10, 11 is not desirable.

Figure 4:
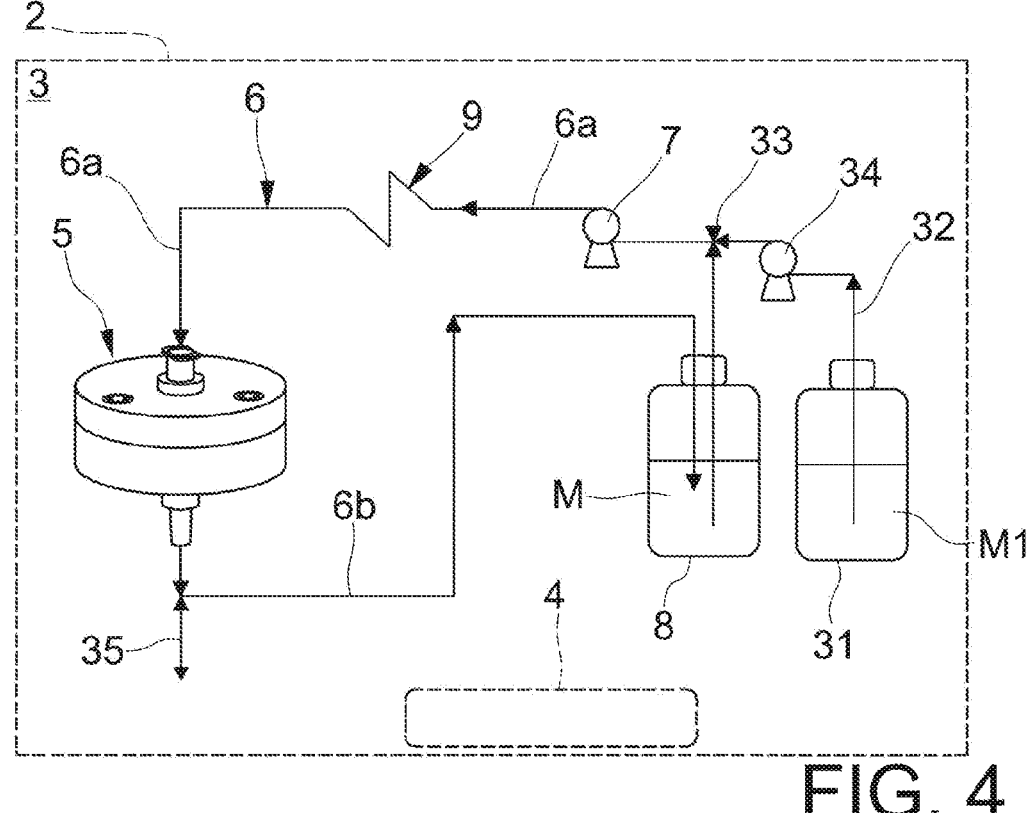
FIG. 4 is a schematic view of yet another version of the apparatus according to the invention, with partial recirculation of the culture medium.

Another embodiment of the apparatus 1 for in vitro culture of reproductive tissues according to the present invention is schematically illustrated in FIG. 4.

Figure 2:
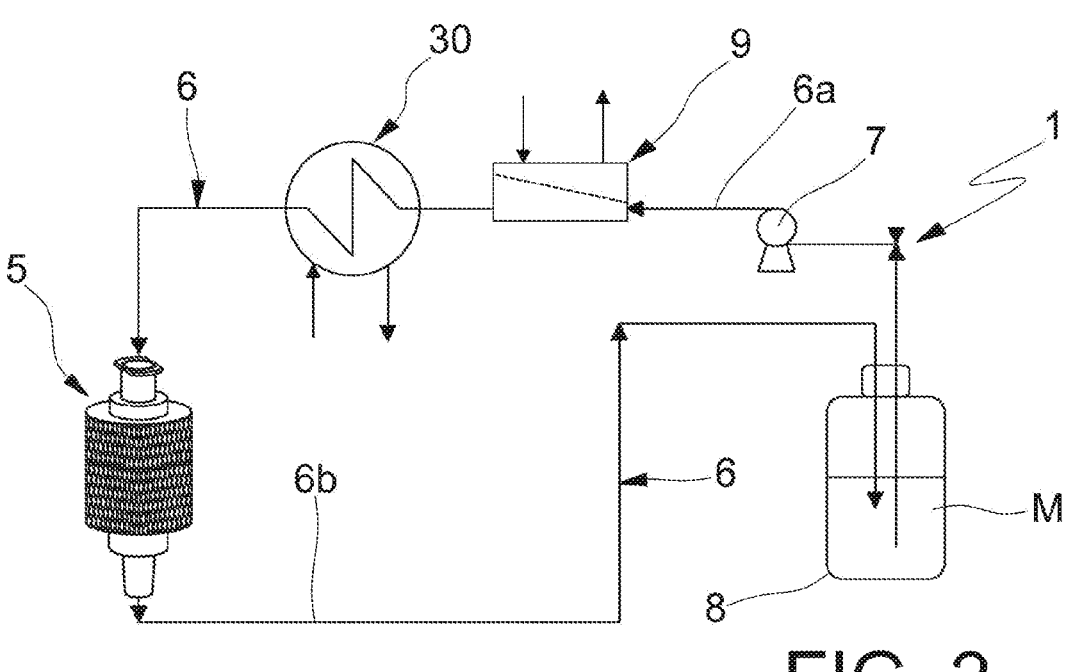
FIG. 2 is a schematic view of another version of an apparatus for the in vitro culture of reproductive tissues according to the present invention, similar to that of FIG. 1 but without incubator.
Figure 3:
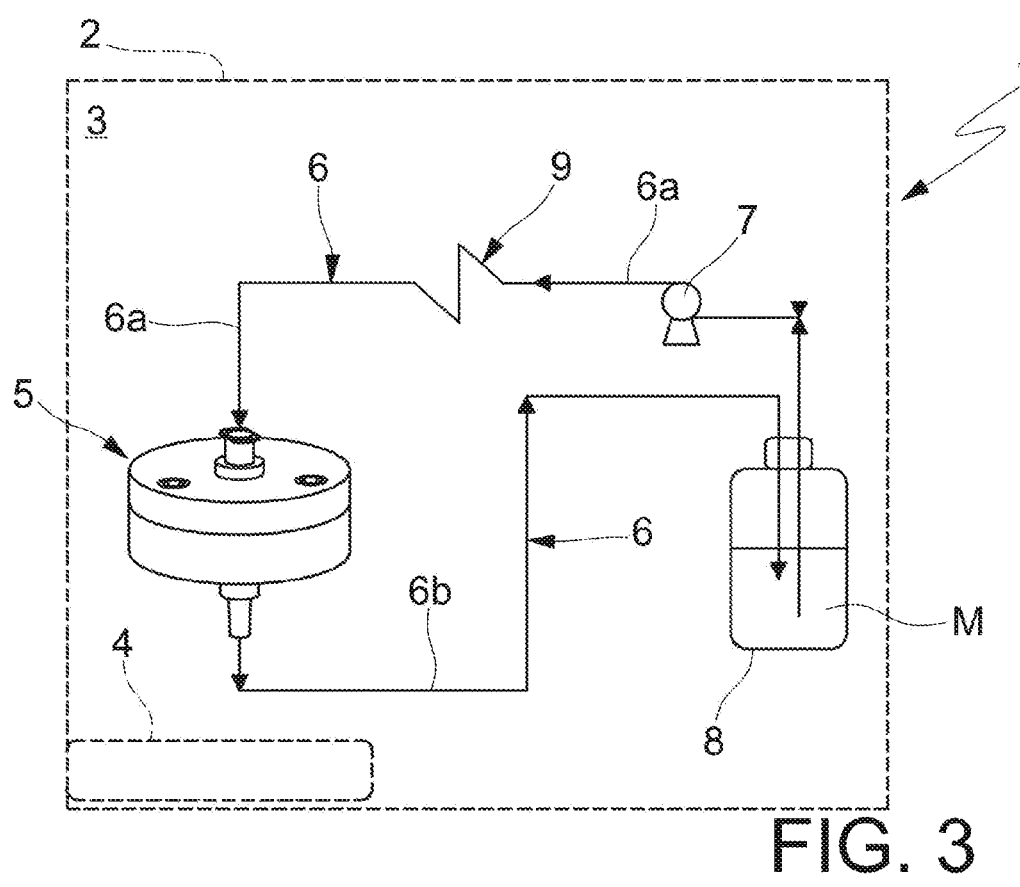
FIG. 3 is a schematic view of another version of the apparatus according to the invention, comprising a different version of the bioreactor.

This embodiment differs from that illustrated in FIG. 3 in that the recirculation of the culture medium M in the circuit 6 is partial, rather than complete, as occurs, however, in the versions of FIGS. 1-3.

The objective of achieving partial, rather than complete, recirculation is to ensure the continuous feeding, along circuit 6, of a given flow rate of a fresh culture medium M1, and to modulate the distribution of the solutes fed as the culture medium inside the bioreactor culture chamber.

For this purpose, the apparatus 1 according to this version comprises an additional tank 31, which precisely contains a fresh culture medium M1.

Furthermore, the apparatus 1 comprises an additional circuit 32 which supplies a given flow rate of the fresh culture medium M1 to the main circuit 6.

More in detail, the additional circuit 32 flows into a suitable fitting 33, provided along the delivery duct 6a, upstream from the pump 7.

An additional pump 34 is also provided along the supplementary circuit 32, which draws the fresh culture medium M1 from the additional tank 31.

According to an aspect of the invention, for a given flow rate of fresh culture medium M1 which is fed to the circuit 6, an equal flow rate of spent culture medium M is removed from the circuit 6.

In particular, the flow of spent culture medium M is removed through an exhaust duct 35.

The exhaust duct 35 is provided at the outlet port 18 of the bioreactor 5 (for example, it can be connected to a fitting provided along the return duct 6b of the circuit 6).

Figure 5:
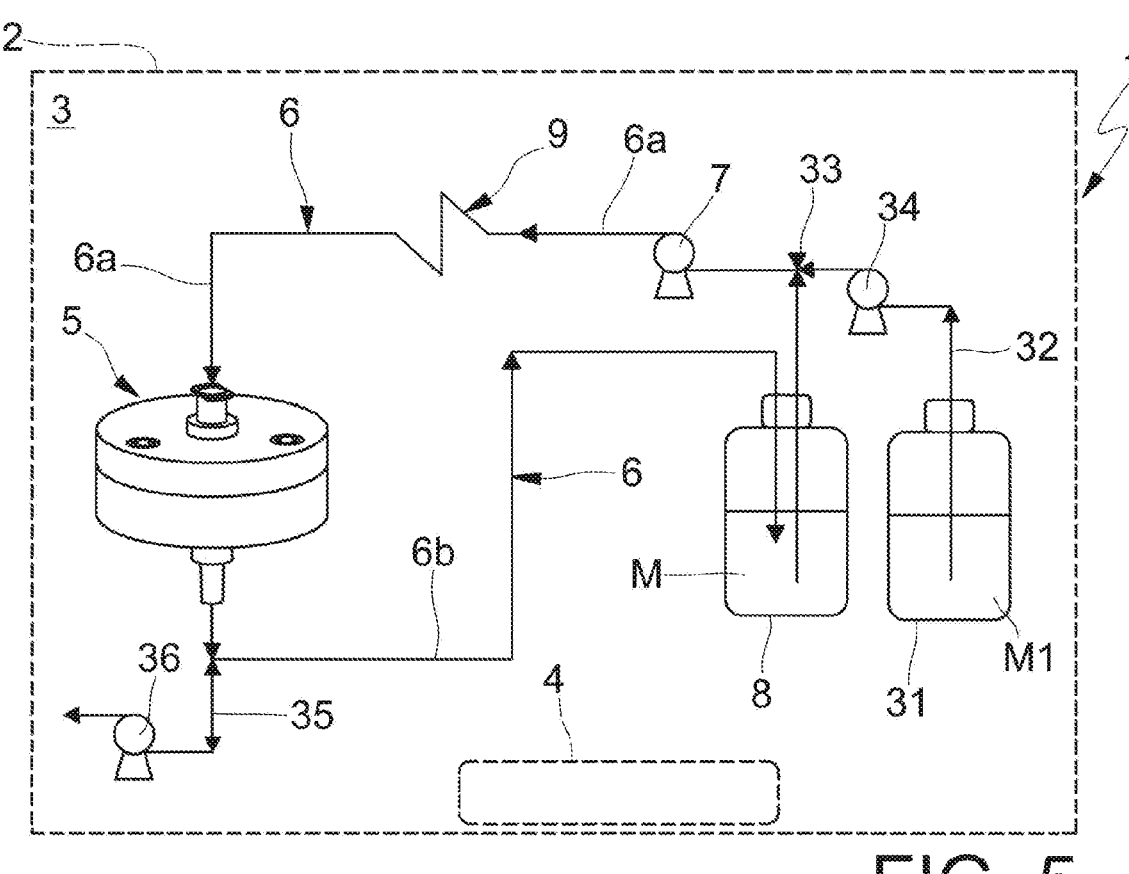
FIG. 5 is a schematic view of yet another version of the apparatus according to the invention, again with partial recirculation of the culture medium.

Another embodiment of the apparatus 1 for in vitro culture of reproductive tissues according to the present invention is schematically illustrated in FIG. 5.

This embodiment differs from that of the previous FIG. 4 in that the apparatus 1 comprises a second additional pump 36, for the removal of the spent culture medium M.

The second additional pump 36 is installed along the exhaust duct 35; it allows to remove the predetermined flow rate of the spent culture medium M in a quick and effective way, thus avoiding the formation of accidental obstructions or other outflow issues along the exhaust duct 35.

Figure 6:
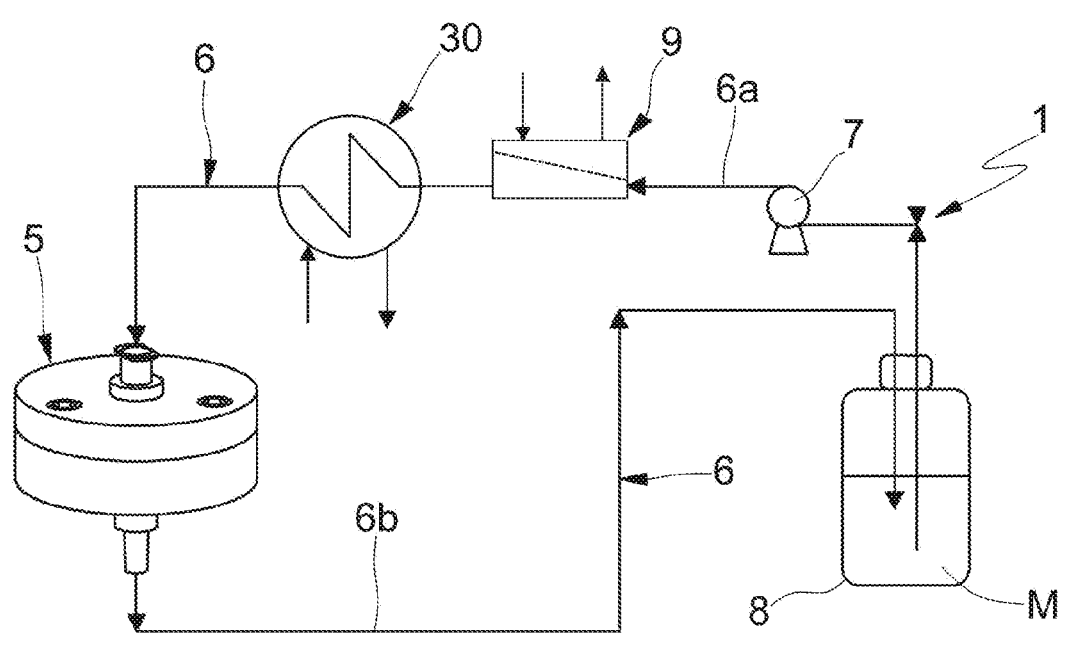
FIG. 6 is a schematic view of another version of an apparatus according to the invention, similar to that of FIG. 3 but without incubator.

Another embodiment of the apparatus 1 for in vitro culture of reproductive tissues according to the present invention is schematically illustrated in FIG. 6.

This embodiment of the invention differs from that illustrated in FIG. 3—and as described with regard to the embodiment of FIG. 2—in that the apparatus 1 has no incubator.

Also in this case, the absence of the incubator is compensated by the fact that the apparatus 1 is completely insulated, and comprises a heat exchanger 30, integrated along the circulation circuit 6 of the culture medium M.

The heat exchanger 30 is integrated, along the delivery duct 6a, immediately downstream of the gas exchanger 9, with reference to the circulation flow of the culture medium M.

The heat exchanger 30 maintains the temperature of the culture medium M within a predetermined range of optimal operation.

In this embodiment of the apparatus 1 the gas exchanger 9 is, by way of example but not limited to, a gas exchanger with hollow capillary membranes for blood oxygenation which allows, for example, to administer to the culture medium M the gaseous oxygen supplied to the gas compartment of the exchanger by means of, but not limited to, a compressed gas cylinder.

This allows to eliminate the need for incubator 2; the heat exchanger 30 can be of any type suitable for this type of application.

The present invention also concerns a process for in vitro culture of fragments of reproductive tissues.

The process comprises a step of providing an apparatus 1 for the in vitro culture of fragments F of reproductive tissues, having the previously described characteristics (in any one of the embodiments according to FIGS. 1-6), wherein the apparatus 1 comprises at least one bioreactor 5

(in the version of FIG. 7, or that of FIG. 8, in relation to the specific embodiment considered).

The process also comprises a step of supplying fragments of reproductive tissue F and placing them inside the culture chamber 12 of the bioreactor 5, positioning them on the porous support 13, interposed between the first network 14 and the second network 15, at mutually predetermined distances.

These mutual predetermined distances allow to obtain, in particular:

a controlled flow of the culture medium M. M1 around each tissue fragment F;

the application of controlled fluid/mechanical forces, which act on the external surfaces of the aforementioned fabric fragments F;

for each fragment F, the sharing, with the other fragments F, of the contents of the culture medium M. M1 and the metabolic by-products of the tissues, at any stage of maturation and growth of the tissues.

The process then comprises a step of starting the apparatus 1, and of feeding the bioreactor 5 with the culture medium M. M1.

More in detail, in this step of the process, the culture medium M. M1 is fed, inside the culture chamber 12 and the circulation circuit 6, in such a way as to determine, on the external surface of the reproductive tissue fragments F, a suitable spatial distribution of the dissolved oxygen concentration in the culture medium M, M1.

This spatial distribution can be constant, or it can be modified intermittently, gradually or continuously over time, or according to a variation process which can be the combination of the above-mentioned ones.

Moreover, in this step of the process, the culture medium M. M1 is fed, inside the culture chamber 12 and the circulation circuit 6, in such a way as to determine, on the external surface of the reproductive tissue fragments F, a suitable spatial distribution of nutrients and waste metabolites.

This spatial distribution can be constant, or it can be modified intermittently, gradually or continuously over time, or according to a variation process which can be a combination of the above-mentioned ones.

Additionally, in this step of the process, the culture medium M. M1 is fed, inside the culture chamber 12 and the circulation circuit 6, in such a way as to determine, on the external surface of the reproductive tissue fragments F, a suitable spatial distribution of biochemical signals, including hormones (but not limited to the latter).

The latter spatial distribution can be constant, or it can be modified intermittently, gradually or continuously over time, or according to a variation process which can be a combination of the above-mentioned ones.

Finally, in this step of the process, the culture medium M. M1 is fed, inside the culture chamber 12 and the circulation circuit 6, in such a way as to determine, on the external surface of the reproductive tissue fragments F, a suitable spatial distribution of biofluid-dynamic signals.

The latter spatial distribution can be constant, or it can be modified intermittently, gradually or continuously over time, or according to a variation process which can be a combination of the above-mentioned ones.

These solutions and measures help the growth and long-term survival of the follicles. In an embodiment of the process according to the invention, the fragments F of reproductive tissue are selected from the group comprising fresh reproductive tissue and cryopreserved reproductive tissue.

In another embodiment of the process according to the invention, the fragments F of reproductive tissue are selected from the group comprising fresh or cryopreserved cortical tissue.

In another embodiment of the process according to the invention, the fragments F of reproductive tissue are selected from the group comprising fresh or cryopreserved medullary tissue.

In yet another embodiment of the process according to the invention, the fragments F of reproductive tissue are selected from the group comprising fresh or cryopreserved ovarian tissue, completely or partially deprived of medullary tissue and/or tunica albuginea, or whose tunic is permeabilized and/or softened by mechanical and/or chemical and/or enzymatic means.

The process may also comprise a step of operating one or more actuators A of the bioreactor 5, provided inside the culture chamber 12, to passively or actively stimulate the fragments F of reproductive tissue, during culture, with controlled mechanical stresses, including (but not limited to) compressive or tensile stresses.

Some examples of application of the culture process are described below, using the apparatus 1, and therefore the bioreactor 5, according to the present invention. In these examples, fragments of primary ovarian tissue are cultured between two warp knit polyester multifilament networks with pores typically measuring 330 microns×290 microns.

The first example concerns the culture of bovine ovarian tissue.

Bovine ovarian tissue fragments F are 1 mm×1 mm×0.5 mm in size.

The culture conditions are as follows:

filling time of the bioreactor: 1.5 mins;

nominal flow of the culture medium: 0.23 mL/(min cm);

tissue volume/bioreactor volume ratio: 0.08%;

maximum local deformation (mechanical stress): 0%;

maximum shearing stress: 3×10' N/m.

For better understanding, the results of the culture obtained with the process according to the invention are compared with situations implying fresh tissue, and culture with conventional plates (inside brackets).

Culture time: 6 days;

Progression of follicles from primordial state to:

primary: 55% (fresh tissue: 18.5%; conventional plates: 75%);

secondary: 41.3% (fresh tissue: 5.2%; conventional plates: 3.6%).

Quality of follicles expressed as a percentage of follicles of a given grade (Grade I being the best, Grade III the worst):

Grade I: 22.3 (fresh tissue: 27.5%; conventional plates: 12.3%);

Grade II: 43.7% (fresh tissue: 42.8%; conventional plates: 36.6%);

Grade III: 34% (fresh tissue: 29.7%; conventional plates: 51.1%).

Vitality: 71.7% (fresh tissue: 79.1%; conventional plates: 53%).

The second example concerns the culture of human ovarian tissue.

Human ovarian tissue fragments F are 1 mm×1 mm×0.5 mm in size.

The results of two different culture conditions are presented.

The first culture conditions are as follows:

filling time of the bioreactor: 1.5 mins;

nominal flow of the culture medium: 0.23 mL/(min cm);

tissue volume/bioreactor volume ratio: 0.08%;

maximum local deformation (mechanical stress): 20%;

maximum shearing stress: 3×10' N/m.

In this case, too, for better understanding, the results of the culture obtained with the process according to the invention are compared with situations implying fresh tissue, and culture with conventional plates (inside brackets).

Culture time: 6 days;

Progression of follicles from primordial state to:

primary: 54.5% (fresh tissue: 21.1%; conventional plates: 75.5%);

secondary: 28.2% (fresh tissue: 3.3%; conventional plates: 3.6%).

Quality of follicles expressed as a percentage of follicles of a given grade (Grade I being the best, Grade III the worst):

Grade I: 33.9% (fresh tissue: 41.2%; conventional plates: 12.3%);

Grade II: 38.2% (fresh tissue: 31.6%; conventional plates: 36.6%);

Grade III: 27.9% (fresh tissue: 27.2%; conventional plates: 51.1%).

Vitality: 66% (fresh tissue: 78.4%; conventional plates: 47%).

The second culture conditions are as follows:

filling time of the bioreactor: 0.5 mins;

nominal flow of the culture medium: 0.41 mL/(min cm);

tissue volume/bioreactor volume ratio: 0.25%;

maximum local deformation (mechanical stress): 60%;

maximum shearing stress: 5×10' N/m.

In this other case, too, for better understanding, the results of the culture obtained with the process according to the invention are compared with situations implying fresh tissue, and culture with conventional plates (inside brackets).

Culture time: 6 days;

Progression of follicles from primordial state to:

primary: 44.1% (fresh tissue: 21.1%; conventional plates: 75.5%);

secondary: 14.1% (fresh tissue: 3.3%; conventional plates: 3.6%).

Quality of follicles expressed as a percentage of follicles of a given grade (Grade I being the best, Grade III the worst):

Grade I: 56.4 (fresh tissue: 41.2%; conventional plates: 12.3%);

Grade II: 13.2% (fresh tissue: 31.6%; conventional plates: 36.6%);

Grade III: 30.4% (fresh tissue: 27.2%; conventional plates: 51.1%).

Vitality: 63.4% (fresh tissue: 78.4%; conventional plates: 47%).

As can be seen from the results of the examples presented, the characteristics of the cultured tissues which are obtained with the application of the process according to the invention are, in some cases, even better than those of fresh tissue.

Furthermore, it is also observed that these characteristics are remarkably better than those of tissues cultured with conventional plates.

In general, the operating parameters of the apparatus may vary as follows:

filling time: from 0.5 to 1.5 mins;

nominal flow of the culture medium: from 0.23 to 0.41 mL/min cm;

tissue volume/bioreactor volume ratio: from 0.08 to 0.25%;

maximum local deformation (mechanical stress): from 0 to 20%;

maximum shear stress: from 0 to 5×10' N/m;

culture time: 3 to 21 days.

It has thus been seen how the invention achieves the intended purposes.

The bioreactor, apparatus and process solutions according to the present invention allow better results to be obtained than those achievable with the equipment and process currently available, from multiple points of view, with simple, economical, and easy to control and manage construction and layout solutions.

The present invention has been described according to preferred embodiments, but equivalent variants can still be conceived without departing from the scope of the appended claims.

The invention claimed is:

1. A bioreactor for the in vitro culture of reproductive tissues, comprising:

a first component and a second component, mutually connected, which define between them at least one culture chamber, said first component comprising an inlet port for introducing a culture medium inside said culture chamber, said second component comprising an outlet port, to allow the outlet of the culture medium from said culture chamber, at least one porous support, provided inside said culture chamber, for supporting fragments of reproductive tissue, and nets, positioned above, and below, the fragments of reproductive tissue, with reference to the vertical, or substantially vertical, position of use of the bioreactor, wherein said bioreactor comprises a first net, able to be positioned under the fragments of reproductive tissue, and therefore above said porous support, and a second net, able to be placed over the fragments of reproductive tissue, said nets being shaped and configured so to maintain a plurality of fragments of reproductive tissue, inside the culture chamber, in respective predetermined spatial positions, and at appropriate mutual distances, and to exert a direct mechanical stress, by deformation, on the fragments, wherein the meshes of said nets have smaller dimensions than those of the fragments, i.e. between 200 microns and 500 microns, and wherein the bioreactor comprises one or more actuators, provided inside said culture chamber, able to passively or actively stimulate the fragments of reproductive tissue, during culture, with controlled fluid and/or mechanical stress, in unison with the stress applied by said nets, said actuators being passive, and comprising ribs whose edges protrude from the inner wall of said first component of the bioreactor, or active, and comprising pressure surfaces actuated by stepper motors, the thickness of said nets being such that, when added to the dimensions, or displacements, of said actuators, they cause the tissue to be subjected to deformations less than 20%.

2. The bioreactor according to claim 1, wherein said first net and/or said second net are made using hollow fibres, wherein a heating or cooling liquid flows to exchange heat and control the temperature of the culture medium inside the bioreactor.

3. The bioreactor according to claim 1, wherein said first net and/or said second net are made using gas-permeable only hollow fibres, for allowing the flowing of a gas containing predetermined concentrations of gaseous oxygen and carbon dioxide, to exchange these gases and control their dissolved concentrations in the culture medium inside the bioreactor.

4. The bioreactor according to claim 1, wherein said porous support, said first net and said second net are packed between said first component and said second component, with one or more interposed sealing gaskets, including of the O-ring type, or other similar type.

5. The bioreactor according to claim 1, wherein the meshes of said nets have dimensions smaller than those of the fragments, so as to retain the fragments of tissue inside said culture chamber, in respective predetermined spatial positions, and at appropriate mutual distances, so as to avoid the formation of preferential or by-pass flows that minimise the contact of the culture medium with the tissue fragments, and to enhance the flow of the culture medium around the fragments, in perifusion mode.

6. The bioreactor according to claim 1, wherein said first component and second component are mutually associated by means of connection means of the resolvable type.

7. An apparatus for the in vitro culture of reproductive tissues, comprising:

at least one bioreactor for the in vitro culture of reproductive tissues including:

a first component and a second component, mutually connected, which define between them at least one culture chamber, said first component including an inlet port for introducing a culture medium inside said culture chamber, said second component including an outlet port, to allow the outlet of the culture medium from said culture chamber, at least one porous support, provided inside said culture chamber, for supporting fragments of reproductive tissue, and nets, positioned above, and below, the fragments of reproductive tissue, with reference to the vertical, or substantially vertical, position of use of the bioreactor, wherein said bioreactor comprises a first net, able to be positioned under the fragments of reproductive tissue, and therefore above said porous support, and a second net, able to be placed over the fragments of reproductive tissue, said nets being shaped and configured so to maintain a plurality of fragments of reproductive tissue, inside the culture chamber, in respective predetermined spatial positions, and at appropriate mutual distances, and to exert a direct mechanical stress, by deformation, on the fragments, wherein the meshes of said nets have smaller dimensions than those of the fragments, comprising between 200 microns and 500 microns, and wherein the bioreactor comprises one or more actuators, provided inside said culture chamber, able to passively or actively stimulate the fragments of reproductive tissue, during culture, with controlled fluid and/or mechanical stress, in unison with the stress applied by said nets, said actuators being passive, and including ribs whose edges protrude from the inner wall of said first component of the bioreactor, or active, and including pressure surfaces actuated by stepper motors, the thickness of said nets being such that, when added to the dimensions, or displacements, of said actuators, they cause the tissue to be subjected to deformations less than 20%, said apparatus for the in vitro culture of reproductive tissues further comprising:

a circuit for the circulation of a culture medium inside said bioreactor;

a pump, mounted along said circuit, able to activate the circulation of the culture medium inside said bioreactor;

a tank, which contains the culture medium, installed along said circuit;

a gas exchanger, installed along the circuit, for allowing gas exchange with the culture medium.

8. The apparatus according to claim 7, comprising an incubator which includes a thermally insulated chamber, inside which said bioreactor is contained, or a heat exchanger, provided along said circuit of circulation of the culture medium.

9. The apparatus according to claim 7, wherein the recirculation of the culture medium is partial, said apparatus comprising an additional tank which contains a fresh culture medium, an additional circuit which feeds a given flow rate of fresh culture medium to the main circuit, and an exhaust duct for the removal of an equal flow rate of spent culture medium.

10. A process for the in vitro culture of reproductive tissues, comprising the steps of:

providing an apparatus for the in vitro culture of reproductive tissues including:

at least one bioreactor for the in vitro culture of reproductive tissues including:

a first component and a second component, mutually connected, which define between them at least one culture chamber, said first component including an inlet port for introducing a culture medium inside said culture chamber, said second component including an outlet port, to allow the outlet of the culture medium from said culture chamber, at least one porous support, provided inside said culture chamber, for supporting fragments of reproductive tissue, and nets, positioned above, and below, the fragments of reproductive tissue, with reference to the vertical, or substantially vertical, position of use of the bioreactor, wherein said bioreactor comprises a first net, able to be positioned under the fragments of reproductive tissue, and therefore above said porous support, and a second net, able to be placed over the fragments of reproductive tissue, said nets being shaped and configured so to maintain a plurality of fragments of reproductive tissue, inside the culture chamber, in respective predetermined spatial positions, and at appropriate mutual distances, and to exert a direct mechanical stress, by deformation, on the fragments, wherein the meshes of said nets have smaller dimensions than those of the fragments, comprising between 200 microns and 500 microns, and wherein the bioreactor comprises one or more actuators, provided inside said culture chamber, able to passively or actively stimulate the fragments of reproductive tissue, during culture, with controlled fluid and/or mechanical stress, in unison with the stress applied by said nets, said actuators being passive, and including ribs whose edges protrude from the inner wall of said first component of the bioreactor, or active, and including pressure surfaces actuated by stepper motors, the thickness of said nets being such that, when added to the dimensions, or displacements, of said actuators, they cause the tissue to be subjected to deformations less than 20%, said apparatus for the in vitro culture of reproductive tissues further comprising:

at least one circuit for the circulation of a culture medium inside said bioreactor;

at least one pump, mounted along said circuit, able to activate the circulation of the culture medium inside said bioreactor;

at least one tank, which contains the culture medium, installed along said circuit;

at least one gas exchanger, installed along the circuit, for allowing gas exchange with the culture medium;

the process for the in vitro culture of reproductive tissues, further comprising the steps of:

providing fragments of reproductive tissue, and inserting them inside the culture chamber of said bioreactor, positioning them on said porous support, interposed between said first net and said second net, at mutual predetermined distances;

starting said apparatus, so as to feed said bioreactor with the culture medium;

providing at least one actuator inside said culture chamber; and operating said actuator to passively or actively stress the fragments of reproductive tissue, during culture, by applying controlled fluid dynamic and/or mechanical stress.

11. The process according to claim 10, wherein said step of feeding said bioreactor with the culture medium is carried out in such a way as to determine, on the external surface of the fragments of reproductive tissue, an appropriate spatial distribution of the concentration of dissolved oxygen in the culture medium, and/or an appropriate spatial distribution of nutrients and waste metabolites, and/or an appropriate spatial distribution of biochemical signals, and/or an appropriate spatial distribution of fluid/mechanical signals.

12. The process according to claim 11, wherein said spatial distribution of oxygen concentration, and/or said spatial distribution of nutrients and waste metabolites, and/or said spatial distribution of biochemical signals, said spatial distribution of fluid/mechanical signals is constant, or can be modified intermittently, gradually or continuously over time, or according to a pattern of variation that can be a combination of the above.

13. The process according to claim 10, wherein said fragments of reproductive tissue are selected from the group comprising fresh reproductive tissue and cryopreserved reproductive tissue, or from the group comprising fresh or cryopreserved cortical tissue, or from the group comprising fresh or cryopreserved medullary tissue, or from the group comprising ovarian tissue, fresh or stored in cryopreservation equipment, completely or partially deprived of medullary tissue and/or tunica albuginea, whose tunica can be permeabilized and softened by mechanical and/or chemical and/or enzymatic means.

* * * * *